United States Patent
Kurashina

(10) Patent No.: US 9,974,731 B2
(45) Date of Patent: May 22, 2018

(54) METHOD FOR PRODUCING FUNCTIONAL LUBRICANT AND PARTICULATE MATERIAL SET USED IN THE METHOD

(71) Applicant: medical arc Co., Ltd., Sakai-shi, Osaka (JP)

(72) Inventor: Atsushi Kurashina, Sakai (JP)

(73) Assignee: Medical Arc Co., Ltd., Osaka (JP)

( * ) Notice: Subject to any disclaimer, the term of this patent is extended or adjusted under 35 U.S.C. 154(b) by 0 days. days.

(21) Appl. No.: 15/623,820

(22) Filed: Jun. 15, 2017

(65) Prior Publication Data

US 2017/0281516 A1 Oct. 5, 2017

Related U.S. Application Data

(63) Continuation of application No. PCT/JP2015/083633, filed on Nov. 30, 2015.

(30) Foreign Application Priority Data

Dec. 17, 2014 (JP) .................. 2014-255483

(51) Int. Cl.
| | |
|---|---|
| *A61K 8/81* | (2006.01) |
| *A61K 8/19* | (2006.01) |
| *A61Q 19/00* | (2006.01) |
| *A61K 8/362* | (2006.01) |

(52) U.S. Cl.
CPC .............. *A61K 8/8147* (2013.01); *A61K 8/19* (2013.01); *A61K 8/362* (2013.01); *A61Q 19/00* (2013.01)

(58) Field of Classification Search
None
See application file for complete search history.

(56) References Cited

U.S. PATENT DOCUMENTS

2011/0014249 A1* 1/2011 Mateu ................. A61K 8/19
424/401

FOREIGN PATENT DOCUMENTS

| JP | 63-310807 A | 12/1988 |
|---|---|---|
| JP | 2005-289884 A | 10/2005 |
| JP | 2013-234134 A | 11/2013 |
| JP | 2013234134 A * | 11/2013 |
| JP | 2014-224094 A | 12/2014 |
| JP | 2014224094 A * | 12/2014 |

OTHER PUBLICATIONS

English Translation of JP2014224094 A. "One-formulation type external preparation for skin." https://patents.google.com/patent/JP2014224094A/en, accessed Aug. 30, 2015. Document originally published in Japanese on Dec. 4, 2014. pp. 1-16 (Year: 2014).*

SM Berge, LD Bighley, DC Monkhouse. "Pharmaceutical Salts." Journal of Pharmaceutical Sciences, vol. 66 No. 1, Jan. 1977, pp. 1-19. (Year: 1977).*

English Translation of JP 2013234134 A. https://patents.google.com/patent/JP2013234134A/en. Document originally published in Japanese on Nov. 21, 2013, Translation obtained on Aug. 30, 2017. pp. 1-15 (Year: 2013).*

* cited by examiner

*Primary Examiner* — Isaac Shomer

(74) *Attorney, Agent, or Firm* — Norris McLaughlin & Marcus, P.A.

(57) ABSTRACT

A method for producing a functional lubricant includes mixing particulate sodium polyacrylate alone with water, adding a particulate carbonate which is any one or more of sodium bicarbonate, sodium carbonate, and calcium carbonate and a particulate carboxylic acid which is any one or more of citric acid, lactic acid, malic acid, tartaric acid, succinic acid, fumaric acid, and maleic acid to the water containing the sodium polyacrylate to produce carbon dioxide, and allowing the sodium polyacrylate to disperse without stirring the water to produce a functional lubricant containing the sodium polyacrylate serving as a sole lubricant base. The weight ratio of the sodium polyacrylate to the carbonate and to the carboxylic acid is from 5:1:1 to 8:1:1.

1 Claim, No Drawings

METHOD FOR PRODUCING FUNCTIONAL LUBRICANT AND PARTICULATE MATERIAL SET USED IN THE METHOD

CROSS-REFERENCE TO RELATED APPLICATIONS

This application claims priority to Japanese Patent Application No. 2014-255483 filed Dec. 17, 2014, the entire contents of which are incorporated herein by reference.

BACKGROUND OF THE INVENTION

1. Field of the Invention

The invention of the present application relates to a method for producing a functional lubricant that is applied to the skin of the human body during massage, for example, and to a particulate material set used in the method.

2. Description of the Related Art

Conventionally, a known functional lubricant has been used for reducing stress on the skin (skin surface) during massage, for example (refer to Japanese Patent Application Laid-open No. 2005-289884, for example). This type of functional lubricant employs the thickening effect of sodium polyacrylate, for example, and is prepared to have an adequate level of viscosity and lubricity by dissolving sodium polyacrylate in water.

Sodium polyacrylate is provided in the form of particulate material. To dissolve sodium polyacrylate in the form of particulate material in water, the sodium polyacrylate is gradually added while stirring water. This process involves a long time until an aqueous solution of sodium polyacrylate is produced that contains sodium polyacrylate uniformly dissolved therein. If a large amount of sodium polyacrylate is added at a time or the stirring of water is stopped halfway, the sodium polyacrylate fails to be dissolved uniformly, leading to lumps or agglomerates formed from the aqueous solution of sodium polyacrylate, resulting in an even longer time for dissolution of the sodium polyacrylate.

SUMMARY OF THE INVENTION

An object of the invention of the present application is to address and ameliorate the above-described situation.

The invention of the present application provides a method for producing a functional lubricant including mixing a particulate material of sodium polyacrylate alone with water, putting a particulate material of carbonate made of any one or more of sodium hydrogen carbonate, sodium carbonate, and calcium carbonate and a particulate material of carboxylic acid made of any one or more of citric acid, lactic acid, malic acid, tartaric acid, succinic acid, fumaric acid, and maleic acid into water containing the sodium polyacrylate to produce carbon dioxide, and dispersing the sodium polyacrylate without stirring the water to produce a functional lubricant containing the sodium polyacrylate serving as a sole lubricant base. The sodium polyacrylate has a mixed proportion on a weight ratio basis of 5 to 8 inclusive where the particulate materials of carbonate and carboxylic acid each have a mixed proportion on a weight ratio basis of 1.

The invention of the present application also includes a particulate material set used in the method for producing a functional lubricant. Specifically, this particulate material set includes the particulate material of carbonate, the particulate material of carboxylic acid, and the particulate material of sodium polyacrylate. The sodium polyacrylate has a mixed proportion on a weight ratio basis of 5 to 8 inclusive where the particulate materials of carbonate and carboxylic acid each have a mixed proportion on a weight ratio basis of 1.

DETAILED DESCRIPTION OF THE PREFERRED EMBODIMENTS

The following describes embodiments in which the invention of the present application is put into practice. Sodium polyacrylate used as a lubricant base for a functional lubricant according to the invention of the present application is acknowledged as a food additive and often used as a thickener or emulsifier. An aqueous solution of sodium polyacrylate, which is alkalescent to neutral, is relatively safe, non-toxic to the human body, almost not irritating at all, and has high viscosity and lubricity. The sodium polyacrylate used in the invention of the present application is provided in the form of particulate material (powdered or granular solid) and has high viscosity when dissolved in water. A preferable viscosity of a 1%-by-weight aqueous solution of sodium polyacrylate to have high lubricity is, for example, 500 mPa·s or higher. In this context, the particulate material preferably has a small particle size. The mixed quantity of sodium polyacrylate ranges from about 0.01% to about 5.0% by weight, and more preferably from about 0.03% to about 3.0% by weight.

Water in which the particulate material of sodium polyacrylate is dissolved can be tap water. To ensure a high quality aqueous solution of sodium polyacrylate, purified water that has high purity achieved through distillation, filtration, ion exchange, or the like is preferably used.

Examples of the carbonate used in the invention of the present application may include sodium hydrogen carbonate (sodium bicarbonate), sodium carbonate, and calcium carbonate. These can be used singly or in combination. Sodium hydrogen carbonate, sodium carbonate, and calcium carbonate are also acknowledged as food additives and are non-toxic to the human body. The carbonate used in the invention of the present application is provided in the form of particulate material (powdered or granular solid).

Examples of the carboxylic acid used in the invention of the present application may include citric acid, lactic acid, malic acid, tartaric acid, succinic acid, fumaric acid, and maleic acid. These can be used singly or in combination. Citric acid, lactic acid, malic acid, tartaric acid, succinic acid, fumaric acid, and maleic acid are also acknowledged as food additives and are non-toxic to the human body. The carboxylic acid used in the invention of the present application is provided in the form of particulate material (powdered or granular solid).

To achieve a functional lubricant that has an adequate level of viscosity and lubricity and contains sodium polyacrylate uniformly dissolved therein, the mixing ratio of carbonate, carboxylic acid, and sodium polyacrylate should be 1:1:8. The inventor of the present invention of this application has confirmed, through experiments, that smaller amounts of carbonate and carboxylic acid than prescribed in the mixing ratio above will result in non-uniform dissolution of sodium polyacrylate and lumps or agglomerates formed from the aqueous solution of sodium polyacrylate. It should be understood that larger amounts of carbonate and carboxylic acid than prescribed in the mixing ratio above will lead to uniform dissolution of sodium polyacrylate. The mixing ratio 1:1:8 of carbonate, carboxylic acid, and sodium polyacrylate is a mere reference.

Preparation of the functional lubricant according to the invention of the present application is carried out as follows, for example. Specifically, a particulate material of sodium polyacrylate is put into a predetermined amount of water. During this process, there is no need to stir the water or gradually add the particulate material of sodium polyacrylate. The particulate material of sodium polyacrylate can be put into water at a time. Thus, sodium polyacrylate is not uniformly dissolved at this stage, and lumps or agglomerates are formed in the water containing sodium polyacrylate.

Next, a particulate material of carbonate and a particulate material of carboxylic acid are put into the water containing sodium polyacrylate in which lumps or agglomerates are formed. The particulate material of carbonate and the particulate material of carboxylic acid may be mixed in advance or provided separately. Thus, the water serves as a solvent, making the carbonate react with the carboxylic acid to produce carbon dioxide (carbon dioxide gas). The foaming action of carbon dioxide causes sodium polyacrylate to dissolve uniformly in water. As a result, an aqueous solution of sodium polyacrylate (functional lubricant) that has an adequate level of viscosity and lubricity and is uniformly dissolved can be simply and surely produced without requiring long hours of work such as stirring or gradual addition.

In particular, since the particulate material of carbonate and the particulate material of carboxylic acid are added to water, the pH (concentration of hydrogen ions) of the aqueous solution of sodium polyacrylate can be adjusted with carbonate and carboxylic acid, which means natural pH can be guaranteed with the pH of the aqueous solution of sodium polyacrylate adjusted for example. It should be understood that even by putting the particulate material of sodium polyacrylate, the particulate material of carbonate, and the particulate material of carboxylic acid into water at a time, the aqueous solution of sodium polyacrylate as described above can be simply and surely produced.

To the functional lubricant according to the invention of the present application, a surfactant, an algefacient, a sedative, a disinfectant, a hormonal agent, a flavoring ingredient, a pigment, a filler, a preservative, or other agents may be further added.

The carbonate, carboxylic acid, and sodium polyacrylate can be packed in a small package, such as a container or a bag, and distributed as a particulate material set made of any one or more particulate materials of sodium hydrogen carbonate, sodium carbonate, and calcium carbonate; any one or more particulate materials of citric acid, lactic acid, malic acid, tartaric acid, succinic acid, fumaric acid, and maleic acid; and a particulate material of sodium polyacrylate. This set enables much more compact storage of the functional lubricant than when distributed in the form of aqueous solution, allowing easy transport and handling. Thus, the particulate material set according to the present embodiment is compact, light-weight, highly portable free from leakage, and easy to use. It only requires water to be added anywhere the user wants to use it. Any two or more of the particulate material of carbonate, the particulate material of carboxylic acid, and the particulate material of sodium polyacrylate may be mixed in advance and packed in a package or they may be separately packed in a package.

Furthermore, in place of the sodium polyacrylate described above, polyethylene oxides (including polyethylene glycol) or a mixture thereof may be used. Polyethylene oxides have properties that are equivalent to those of sodium polyacrylate.

EXAMPLES

As a result of experiments carried out based on a broad area of knowledge, the inventor of the present invention of this application has confirmed that a functional lubricant that has an adequate level of viscosity and lubricity and contains sodium polyacrylate uniformly dissolved therein can be produced under the conditions described below. Specifically, particulate materials of sodium polyacrylate, sodium hydrogen carbonate, and citric acid were put into 500-ml water, and a functional lubricant as an aqueous solution containing 1%-by-weight sodium polyacrylate was prepared. The mixed quantity of sodium polyacrylate was 5.0 g, the mixed quantity of sodium hydrogen carbonate was 0.625 g, and the mixed quantity of citric acid was 0.625 g. In other words, the mixing ratio of sodium hydrogen carbonate, citric acid, and sodium polyacrylate was 1:1:8. The particulate material of sodium polyacrylate was uniformly dissolved several seconds to several tens of seconds after the particulate materials of sodium hydrogen carbonate and citric acid were input. The prepared functional lubricant was enclosed in an airtight container and kept for about 30 days. After this period, uniform dissolution of sodium polyacrylate in the aqueous solution was preserved, with adequate levels of viscosity, lubricity, and functionality maintained.

Furthermore, it was confirmed that when a 5.0-g particulate material of sodium polyacrylate, a 0.5-g particulate material of sodium hydrogen carbonate, and a 0.5-g particulate material of citric acid were put into 500-ml water, lumps were formed in a 1%-by-weight aqueous solution of sodium polyacrylate. It was also confirmed that when a 5.0-g particulate material of sodium polyacrylate, a 1.0-g particulate material of sodium hydrogen carbonate, and a 1.0-g particulate material of citric acid were put into 500-ml water, a 1%-by-weight aqueous solution of sodium polyacrylate was uniformly dissolved.

The invention claimed is:

1. A method for producing a functional lubricant comprising:
adding a particulate sodium polyacrylate alone to water without stirring the water thereby to form lumps or agglomerates of the sodium polyacrylate, adding to the water containing the lumps or agglomerates of the sodium polyacrylate, without stirring the water containing the lumps or agglomerates of the sodium polyacrylate, a particulate carbonate which is any one or more of sodium bicarbonate, sodium carbonate, and calcium carbonate and a particulate carboxylic acid which is any one or more of citric acid, lactic acid, malic acid, tartaric acid, succinic acid, fumaric acid, and maleic acid to produce carbon dioxide thereby to cause a foaming action in the water containing the lumps or agglomerates of sodium polyacrylate, the foaming action alone causing the lumps or agglomerates of the sodium polyacrylate to disperse and dissolve in the water to produce a functional lubricant containing the sodium polyacrylate serving as a sole lubricant base, wherein
the weight ratio of the particulate sodium polyacrylate to the particulate carbonate and the particulate carboxylic acid is from 5:1:1 to 8:1:1.

\* \* \* \* \*